(12) United States Patent
Sourdille

(10) Patent No.: US 10,905,589 B2
(45) Date of Patent: Feb. 2, 2021

(54) INTERPOSITIONAL OPHTHALMOLOGICAL IMPLANT

(71) Applicant: Philippe Sourdille, Liniers (FR)

(72) Inventor: Philippe Sourdille, Liniers (FR)

( * ) Notice: Subject to any disclaimer, the term of this patent is extended or adjusted under 35 U.S.C. 154(b) by 336 days.

(21) Appl. No.: 15/562,333

(22) PCT Filed: Mar. 25, 2016

(86) PCT No.: PCT/FR2016/050696
§ 371 (c)(1),
(2) Date: Sep. 27, 2017

(87) PCT Pub. No.: WO2016/156727
PCT Pub. Date: Oct. 6, 2016

(65) Prior Publication Data
US 2018/0353329 A1 Dec. 13, 2018

(30) Foreign Application Priority Data
Mar. 31, 2015 (FR) ..................... 15 52732

(51) Int. Cl.
*A61F 9/007* (2006.01)
(52) U.S. Cl.
CPC .. *A61F 9/00781* (2013.01); *A61F 2250/0009* (2013.01)
(58) Field of Classification Search
CPC ............................ A61F 9/000781
See application file for complete search history.

(56) References Cited

U.S. PATENT DOCUMENTS

| 4,521,210 A * | 6/1985 | Wong ................. A61F 9/00781 604/8 |
| 5,704,907 A | 1/1998 | Nordquist |
| 5,879,319 A * | 3/1999 | Pynson .............. A61F 9/00781 604/8 |
| 7,207,965 B2 * | 4/2007 | Simon ................ A61F 9/00781 604/8 |
| 2004/0015140 A1 | 1/2004 | Shields |
| 2004/0092856 A1 | 5/2004 | Dahan |
| 2004/0193262 A1 * | 9/2004 | Shadduck .......... A61F 9/00781 623/4.1 |

(Continued)

FOREIGN PATENT DOCUMENTS

| JP | 2007526013 | 9/2007 |
| WO | 2012071476 | 5/2012 |

OTHER PUBLICATIONS

International Search Report dated Jun. 9, 2016.
Office Action dated Aug. 5, 2019.
Japanese Office Action dated Dec. 17, 2019.

*Primary Examiner* — Leslie R Deak
(74) *Attorney, Agent, or Firm* — Ipsilon USA, LLP

(57) ABSTRACT

The invention relates to a permanent interpositional ophthalmological implant between the sclera and the uveal tis-sue. The implant comprises a thin uvea-compatible body (50) having a thickness (e) which is at least less than IO times the smallest of the two other dimensions of the body, the body of the implant comprising two opposing edges separated from one another along one of the two dimensions perpendicular to the thickness, and one of the edges, known as the front edge (52), being curved in a concave manner away from body in a plane perpendicular to the thickness.

32 Claims, 6 Drawing Sheets

(56) References Cited

U.S. PATENT DOCUMENTS

2012/0089072 A1* 4/2012 Cunningham, Jr. ........................ A61F 9/00781
604/9

* cited by examiner

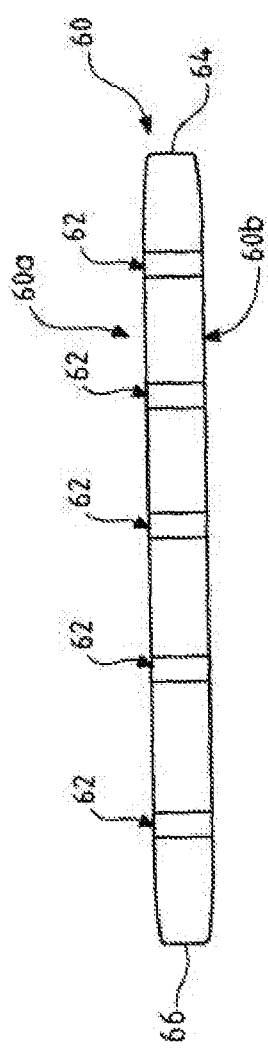
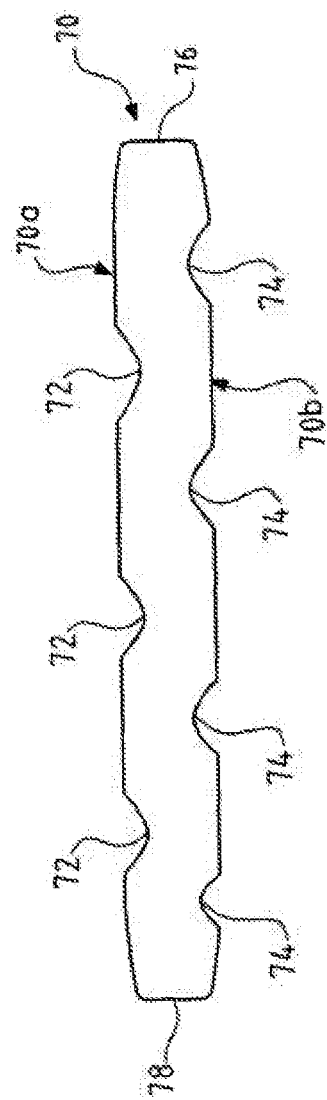
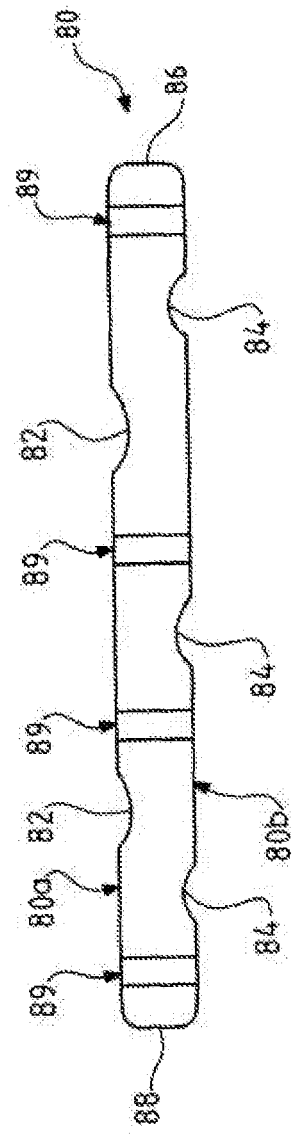

INTERPOSITIONAL OPHTHALMOLOGICAL IMPLANT

RELATED APPLICATION

This application is a National Phase of PCT/FR2016/050696, filed on Mar. 25, 2016 which in turn claims the benefit of priority from French Patent Application No. 15 52732, filed on Mar. 31, 2015, the entirety of which are incorporated by reference.

BACKGROUND

Field of the Invention

The invention relates to an interpositional ophthalmological implant intended to keep the sclera and the ciliary body permanently separated from one another in order to lower intraocular pressure (IOP).

Description of Related Art

Intraocular pressure is the result of an equilibrium reached between its secretion by the ciliary body and its flow through the corneoscleral trabecular meshwork via the Schlemm's canal and its clearance to the aqueous veins and general circulation. A fraction representing 10 to 15% of this flow flows directly through the ciliary trabeculum between the sclera and the ciliary body, and this is what is referred to as the uveo-scleral flow. The longitudinal fibers of the ciliary muscle, particularly during accommodation, play a role in tensioning the trabecular meshwork, facilitating the uveo-scleral flow of the aqueous humor.

In glaucoma, the flow of aqueous humor is reduced at the level of the trabeculum, and this in most cases leads to an increase in intraocular pressure (IOP). Lowering this IOP is therefore the key factor in the medical and/or surgical treatment of glaucoma. Surgical treatment relies on two options: reducing the production of aqueous humor produced by the ciliary body (cyclo-weakening) or increasing the flow of aqueous humor by diverting it. This diversion is performed in different ways:

by making the anterior chamber communicate directly with the suprachoroidal space (cyclodialysis and technical derivatives thereof), but the effect obtained is usually transient and insufficient. By disinserting the insertion of the ciliary muscle in the scleral spur this implantation technique eliminates the physiological mechanism for the uveo-scleral flow in the surgical zone. In addition, post-operative fibrosis extends beyond this zone. It is also known that the part of the implant situated in the anterior chamber may, even if only intermittently, affect the corneal endothelium, thereby leading to a significant risk of evolving corneal edema.

by incising the trabeculum, working from the anterior chamber, as far as the Schlemm's canal in order to short-circuit the trabecular obstacle. This intervention may be supplemented by the insertion into the canal of a stent open toward the anterior chamber in order to maintain permanent direct access for the aqueous humor to the canal. Once again, the results are often partial and temporary, and do not obviate the need for a continuation or resumption of medical treatment.

Filtration surgery is most often used and seeks to divert the aqueous humor under the conjunctiva in order to achieve the necessary drop in pressure. It may create a full-thickness permanent hole in the trabeculum under a scleral flap: this is known as a trabeculectomy. It may also leave the internal part of the trabeculum in place, and this is what is referred to as non-penetrating trabecular surgery (deep sclerotomy, viscocanalostomy). However, filtering surgery runs into complications connected with the insufficiency of the filtering by fibrosis of the filtration bubble (the filtration bubble is present between the sclera and the conjunctiva which finds itself raised) or, conversely, connected with excessively good performance of this filtering.

In this type of surgery around 70% of the surgical successes (which are defined as those achieving a sufficient lowering of the IOP) are found to exhibit, in addition to the sub-conjunctival filtering, an increase in the uveo-scleral flow, which becomes visible on ultrasound examination. Because this increase is one of the mechanisms for lowering the IOP, it is advantageous to be able to induce it surgically.

WO 2010/088258 discloses the implantation, from the anterior chamber and into the space between the sclera and the ciliary body, or even the choroid (the suprachoroidal space), a draining implant the stiffness of which is capable of deforming the surrounding tissues.

The reduction in IOP obtained by these techniques is often insufficient and temporary. Usually it entails resumption or the maintaining of one or more hypotensive medical treatments.

OBJECTS AND SUMMARY

Given the foregoing, the present invention proposes to increase and render permanent the hypotensive effect of the physiological uveo-scleral flow by interposing, between the sclera and the ciliary body, an implant which does not adversely affect the anatomical structures, with or without added intervention, filtering or otherwise.

The subject of the present invention is therefore a permanent interpositional ophthalmological implant between the sclera and the uveal tissue, characterized in that the implant comprises a body with uveal biocompatibility, formed as a single part, the thin body having a substantially uniform single thickness which is at least less than 10 times the smaller of the other two dimensions of the body, the body of the implant comprising two opposite edges which are distant from one another along one of the two dimensions perpendicular to the thickness, one of the two edges, referred to as the anterior edge having, in projection in a plane perpendicular to the thickness, a concave curvature facing toward the outside of the body.

The concave anterior edge of the body of the implant allows said anterior edge to be positioned as close as possible to the trabeculum and on a circumference, thereby allowing the implant to perform its separating effect at the best possible location (the concavity of the anterior edge is generally matched to the radius of the cornea). This configuration of the concave anterior edge allows the aqueous humor to be collected permanently as close as possible to the region of the uveo-scleral flow. Such an implant thus provides a significant improvement in the increase in physiological uveo-scleral flow.

The body of the implant may, in projection in a plane perpendicular to the thickness, have an external peripheral contour the geometry of which is convex with the exception of the portion of the body that comprises the concave anterior edge. The remaining portion of the body in projection in this plane has a convex geometry, which means to say that whenever two points A and B of this remaining portion are considered, the segment AB connecting them is entirely contained within said remaining portion. In other words, outside of the portion of the body that includes the concave anterior edge (this portion may be delimited, on one side, by the concave anterior edge and, on the opposite side, by a straight line internal to the body and which is tangential to the vertex of the concave curvature of the edge and by two opposite edges which are each adjacent to the concave anterior edge and to the tangential straight line) in projection in said plane the remaining portion of the body has no hollows or bosses or reentrant angles or reentrant parts.

Moreover, the thickness of the body is a single thickness in so far as the body is not formed of several parts each having a different thickness and which would give the body a variable-thickness profile (e.g. a stepped profile, a staged or crenelated profile). The body is formed of one single part in so far as it is homogeneous and does not have a complex shape (with cutouts, recesses, returns, etc.) with local variations in geometry both in terms of the thickness and perpendicular to the thickness.

In general, the body on each of its pairs of opposing faces has a planar or overall curved shape with a single curvature, which means to say that such a shape with waviness or saw-teeth is excluded.

The body does not generally have a shape with cutouts, notably in a view in projection in a plane perpendicular to the thickness.

In general, the overall shape of the body is simple compared with the shapes of the bodies of implants of the prior art.

More specifically, the body of the implant according to the invention is different from the body of the implant of documents WO 95/35078 (body with two parts of different thickness and with different widths perpendicular to the thickness), U.S. Pat. No. 4,521,210 (cross-shaped body with one branch longer than the others), U.S. 2004/0015140 (spatula-shaped body with an anterior portion the width of which is reduced in comparison with the rest of the body and with lateral cutouts and an axial posterior cutout for the insertion of a tool for installing the implant) and U.S. 2004/0092856 (T-shaped body with the two opposite ends of the cross bar of the T of a thickness greater than that of the remaining part of the T).

The body of the implant is intended to separate the sclera and the uveal tissue from one another so that it becomes permanently interposed between them (creating a permanent space), thus creating a zone in which there is lower resistance to the flow of the aqueous humor. A thin body as described hereinabove affords sufficient separation of the overlying and underlying structures (sclera and uveal tissue) to effectively drain the physiological uveo-scleral flow.

What is meant by uveo-compatible body is a body the constituent material or materials of which do not erode or denature the surrounding ocular structures, in this instance the structures of the uvea. Their biocompatibility of the body is not, on its own, enough for the body to be able to be implanted permanently in the uvea, more particularly between the sclera and the uveal tissue.

According to other possible features considered in isolation or in combination with one another:

the body is for example thinned at the anterior edge, with respect to the remainder of the body, so as to be able to be inserted under the scleral spur, as close as possible to the trabeculum without, however, disturbing the structure of the scleral spur;

more particularly, the concave anterior edge is thinned over a dimension comprised between 100 and 400 µm, this dimension being considered in a direction extending between the two opposite edges of the body; this distance over which the anterior edge is thinned affords good results in terms of the efficiency of positioning of the implant as close as possible to the trabeculum without however disturbing the structure of the scleral spur; the opposite posterior edge has, for example, a thickness identical to the rest of the body of the implant; the body thus maintains a substantially uniform thickness (within the possible local variations in thickness of the body) over the part that does not comprise the thinned edge (when a thinned edge is present);

the two opposite edges of the body, namely the anterior edge and the opposite posterior edge, are distant from one another along the smaller of the two dimensions perpendicular to the thickness;

the concave curvature of the anterior edge has a radius of curvature between 5 and 7 mm; such a radius of curvature of the anterior edge allows this edge to be positioned concentrically with the corneal margin (the transition between the cornea and the sclera), thus ensuring maximum possible collection of aqueous humor;

the body of the implant is elastically deformable so that it can be bent without inducing permanent deformation so that it can be handled using a micro instrument, or injected using an ophthalmological injection system; in the state of rest, the nondeformed body is planar and, once permanently implanted between the sclera and the uveal tissue, it is deformed into a state referred to as the deformed state of use; it then conforms as closely as possible to the curvatures of the sclera and of the ciliary body;

the body of the implant comprises, in a deformed state in which it is capable of being used as an interpositional ophthalmological implant between the sclera and the uveal tissue, another concave curvature in a direction perpendicular to a plane defined by the two dimensions of the implant which are perpendicular to the thickness; this second curvature allows it to conform as closely as possible to the curvature of the ciliary body by molding itself to a portion of the sphere of the eye (underlying ciliary body); the implant thus has a double curvature;

the body of the implant is made from a material which has a Young's modulus of between 30 and 60 kg/cm$^2$; this rigidity/flexibility characteristic allows the body to deform elastically as it is being inserted into the eye and then be kept in a deformed state permanently by the overlying and underlying structures of the eye, following the natural curvatures of these structures (excessive rigidity of the body would actually induce deformations in these structures that could impair their function(s)); it will be noted that the above-defined rigidity is lower than that of the sclera (or even very much lower), thereby allowing the implant to line the sclera without deforming it;

the body of the implant is not elastically deformable and permanently comprises a second concave curvature in a direction perpendicular to a plane defined by the two dimensions of the implant which are perpendicular to the thickness; the concave second curvature is chosen to follow the natural curvatures of the overlying and underlying structures of the eye between which the body is implanted;

the second concave curvature has a radius of curvature of between 10 and 15 mm; this radius of curvature is particularly well suited to allowing the body of the implant to mold to the spherical portion of the underlying ciliary body;

the body of the implant has, in a three-dimensional view, the overall shape of a spherical cap portion;

the body of the implant is able to allow a liquid flow of aqueous humor through said body and/or along same; the implant interposed between the ciliary body and the sclera needs to encourage the flow of the aqueous humor collected at the level of the trabeculum toward the posterior part of the eye, whether this be along the body (from its anterior edge to its opposite posterior edge) and/or through the body;

the body of the implant has two large opposite faces separated from one another along the thickness of the body; the two large opposite faces are generally mutually parallel and have the same curvature at rest and/or when the implant is implanted (the two large opposite faces may effectively be curved only after implantation);

the two large opposite faces are substantially planar or curved;

the two large opposite faces each have one or several local variations in thickness of between 10 and 20 μm; these local variations in thickness occur along one or two dimensions perpendicular to the thickness which are small in comparison with the dimension or dimensions of the body perpendicular to the thickness (about 10 times smaller than the dimension or dimensions); it will also be noted that the possible variation in thickness is of the order of 10% of the uniform overall thickness of the body; thus, a substantially uniform thickness is to be understood as meaning a thickness which has a given nominal or overall value and which locally tolerates one or more variations in thickness as defined hereinabove;

the body of the implant is pierced with orifices passing through its thickness; these orifices allow the passage of a flow of aqueous humor through the body;

the body of the implant comprises, on at least one of its two large opposite faces, a relief which is able to encourage a flow of aqueous humor along said at least one large face;

the relief on said at least one large face of the body takes the form of grooves formed on said at least one large face or of roughnesses conferred thereon; this relief may for example adopt the form of grooves or channels arranged on the surface substantially parallel to a direction that extends from the anterior edge of the body to the opposite posterior edge thereof;

the body of the implant comprises at least one material chosen from the following materials: PTFE, polysiloxane, hydrophilic or hydrophobic acrylate hydrogels;

the body of the implant has, when viewed in a plane containing the projections of the two largest dimensions of said body, dimensions comprised between minimum dimensions of 2×2 mm and maximum dimensions of 7×7 mm; compliance with these dimensions allows the implant to guarantee the desirable uveo-scleral flow action: the minimum dimensions guarantee that a sufficient interpositional effect will be obtained that will decrease the resistance to flow and the maximum dimensions mean that the dynamics of the aqueous humor are not disturbed by too great a flow (such disturbance would carry the risk of leading to ocular hypotony);

the thickness of the body of the implant is between 50 and 400 μm; such a thickness offers effective separation;

the body of the implant has a volume of between 0.8 and 8 mm$^3$; such a volume makes it possible to increase the uveo-scleral flow but not to excess;

the body of the implant has properties of releasing one or more substances;

the body has an external surface which exhibits neither sharp edges nor sharp corners; the external surface thus has only rounded corners or edges (whatever the spatial orientation, namely in projection in a plane perpendicular to the thickness or in a plane including the direction in which the thickness extends) to make the implant easier to install and to remove any potential for trauma to the surrounding tissues;

the body has, viewed in projection in a plane perpendicular to the thickness, four edges or sides delimiting the outline of said body: the anterior edge and the opposite posterior edge, and two lateral edges adjacent to said anterior and posterior edges and which connect the latter edges to one another (four-sided polygon);

the two lateral edges converge toward one another in a direction leading from the posterior edge toward the anterior edge (the anterior edge being shorter than the posterior edge) or are mutually parallel.

the body has, viewed in projection in a plane perpendicular to the thickness, the overall shape of an annular segment.

BRIEF DESCRIPTION OF THE DRAWINGS

Further features and advantages will become apparent during the course of the following description given solely by way of nonlimiting example and made with reference to the attached drawings in which:

FIGS. 3, 4 and 5 each schematically illustrate one possible embodiment of a configuration of an implant which encourages the flow of aqueous humor through (FIG. 3), along (FIG. 4), through and along (FIG. 5) the body of an implant according to the invention;

DETAILED DESCRIPTION

Figure 1:
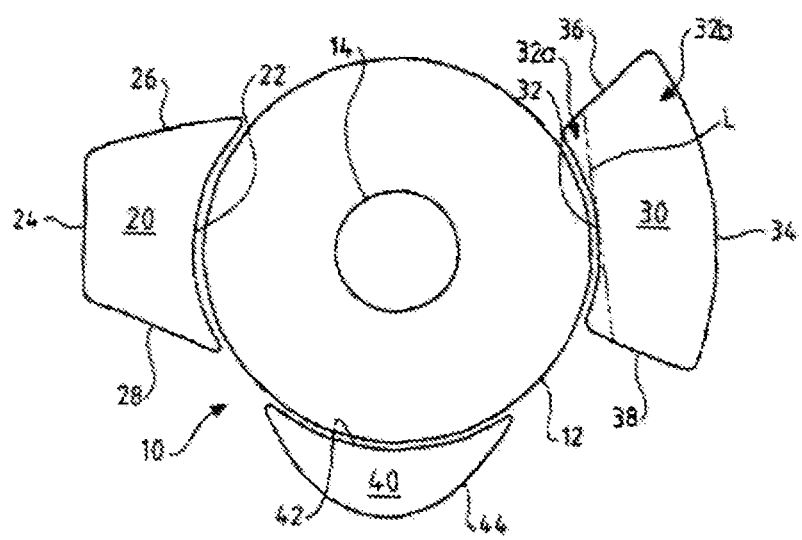
FIG. 1 is a very schematic general view showing, in front view, several possible embodiments of implants according to the invention, positioned around the cornea of an eye.

The invention relates to an ophthalmological implant which is intended to be implanted permanently between the sclera and the uveal tissue and has therefore been interposed permanently between these.

The implant according to the invention comprises a body that is thin so that, once interposed between the sclera and the uveal tissue, it does not deform the overlying and underlying tissues to an inacceptable extent. An acceptable deformation of the tissues is a deformation that does not impair the function or functions of either one or both of these tissues.

The body of the implant has three dimensions in space: a thickness, a length and a width which are perpendicular to the thickness (or two identical dimensions if the length and the width are equal). What is to be understood by "thin body" is a body the thickness of which is at least less than 10 times the shortest of the other two dimensions of the body, namely the width, or either one of the two other dimensions if these are equal. In one exemplary embodiment, the thickness is less than 13 times the width of the body. By way of example, for a body with dimensions (width and length) of 4×5 mm, its thickness is 0.3 mm.

The body of the implant comprises two opposite edges which are distant from one another in one of the two dimensions perpendicular to the thickness, for example the width (the smaller of the two dimensions).

One of the two distant edges is referred to as the anterior edge and has, in projection in a plane perpendicular to the thickness, a concave curvature facing towards the outside of the body.

The concave curvature of the anterior edge allows this edge of the implant to be positioned as close as possible to the trabeculum, namely in the zone of the uveo-scleral flow, so as to collect the greatest possible quantity of aqueous humor.

The radius of curvature of the concave edge is, for example, comprised between 5 and 7 mm, this allowing this edge to be positioned concentrically with the corneal margin, and therefore as close as possible to the trabeculum. The concentricity is defined with respect to the center of the cornea (the center of the circle) which is not always aligned with the center of the pupil. The radius of curvature is, for example, equal to 5.5 mm.

The other opposite edge is referred to as the posterior edge and is not necessarily curved (convexity facing toward the outside) in a plane perpendicular to the thickness. Indeed it may be rectilinear or even adopt a different shape.

The body of the implant comprises at least one material which is known for its uveo compatibility properties and the body is thus uveo-compatible. Such properties give the body very low adhesion to the ocular tissues. In other words, said at least one material is not liable to adversely affect the overlying and underlying structures as a result of the body coming into contact with these structures and as a result of their repeated movements over time.

In general, the body of the implant may, in projection in a plane perpendicular to the thickness, exhibit an external peripheral contour with convex geometry with the exception of the portion of the body which comprises the concave anterior edge. The remaining portion of the body in projection in this plane has a convex geometry, which means to say that whenever two points A and B of this remaining portion are considered, the segment AB that connects them is entirely contained in said remaining portion. In other words, outside of the portion of the body that includes the concave anterior edge (this portion may be delimited on one side by the concave anterior edge and on the opposite side by an imaginary straight line internal to the body and which runs tangentially to the vertex of the concave curvature of the edge and by two opposite edges each of which are adjacent to the concave anterior edge and to the tangential line) in projection in said plane the remaining portion of the body has no recesses or bosses or reentrant angles or reentrant parts.

Moreover, the thickness of the body is a single thickness in so far as the body is not formed of several parts each having a different thickness and which would give the body a variable-thickness profile (e.g.: stepped profile, staged profile, or square-wave profile).

In general, the body on each of its opposite pairs of faces has a planar or curved overall shape with one single curvature, which means to say that such a shape with waviness or a saw-toothed shape is excluded.

The body generally does not have a shape with cutouts, notably when viewed in projection in the plane perpendicular to the thickness.

As depicted in FIG. 1, an eye 10 is depicted in front-on view very schematically by the cornea 12 with the pupil 14 at the center.

Three possible forms of embodiment of an ophthalmological implant according to the invention are depicted in implanted position around the cornea in a view in projection in a plane perpendicular to the thickness of the body (plane of FIG. 1).

These three possible forms of implant, referenced 20, 30 and 40, each have in common a concave anterior edge 22, 32, 42 of which the concavity, which means to say the radius of curvature, is adjusted so that said edge can be arranged concentrically with the corneal margin, namely as close as possible to the trabeculum.

These three implants each have an opposite posterior edge 24, 34, 44 different from the anterior edge and lateral edges that differ from one implant to another.

The posterior edge 24 of the implant 20 is rectilinear and the body comprises two lateral edges 26, 28 adjacent to the anterior and posterior edges and connecting the latter to one another; the lateral edges 26, 28 diverge relative to one another from the posterior edge toward the anterior edge in so far as the anterior edge 22 is longer than the posterior edge 24; the lateral edges 26, 28 are symmetric with respect to one another although, in an alternative form that has not been depicted, they could be asymmetric with respect to one another.

The posterior edge 34 of the implant 30 is convex (convexity facing toward the outside of the body; alternatively, the posterior edge may be rectilinear) and the radius of curvature may or may not be identical to that of the concave edge 32. The body comprises two lateral edges 36, 38 adjacent to the anterior and posterior edges and connecting these together; the lateral edges 36, 38 converge toward one another from the posterior edge toward the anterior edge in so far as the anterior edge 32 is shorter than the posterior edge 34. In general, the body of the implant 30 when viewed from above (perpendicular to its thickness) has a shape reminiscent of a trapezoid the base of which is concave and the top of which is convex or resembles an annular segment or portion extending over a given angular sector.

The body of the implant 30 here has, in projection in a plane perpendicular to the thickness, an external peripheral contour with a convex geometry with the exception of the portion 32a of the body which comprises the concave anterior edge 32. The remaining portion 32b of the body in projection in this plane has a convex geometry, which means to say that each time two points A and B of this remaining portion are considered, the segment AB that connects them is entirely contained in said remaining portion. This portion is delimited, on one side, by the concave anterior edge 32, on the opposite side, by a straight line or imaginary axis L internal to the body and which runs tangential to the vertex of the concave curvature of the edge (of the side of the convexity of the curvature) and by two opposite edges each of which is adjacent to the concave anterior edge and to the straight line or tangential axis L. In other words, outside of the portion 32a of the body which includes the concave anterior edge, in projection in said plane the remaining portion of the body has no hollows or bosses or reentrant angles or reentrant parts. It will be noted that other convex geometries may be envisioned for the body.

According to an alternative form which has not been depicted, the lateral edges may be parallel to one another. According to another alternative form which has not been depicted, the overall shape of the body when viewed from above may be that of a rectangle with the exception of the concave anterior edge, it being possible for the posterior edge to be rectilinear or convex.

The convex posterior edge 44 of the implant 40 (convexity facing toward the outside of the body) is joined directly to the anterior edge 42; there are no adjacent lateral edges; the body thus has the overall shape of a crescent when viewed from above (FIG. 1) and thus exhibits, between the two, anterior 42 and posterior 44, edges a dimension that is relatively small in comparison with the implants 20 and 30 in which the two edges are more widely spaced from one another. The shape of the implant 40 makes it easier to insert through an incision of a smaller size than for the implants 20 and 30, while at the same time prolonging the effect of separation toward the rear (posterior edge).

With certain configurations of implant it is envisioned that the length of the anterior edge be maximized, the configuration and/or length of the posterior edge themselves being more free.

It should be noted that, in general, the lateral edges of the implant (when there are any, which there are not in the case of the implant 40 of FIG. 1) can be arranged radially as with the implant 30 (edges radial relative to the center of the imaginary circle with respect to which the concave edge of the implant is positioned; the edges thus converge toward the center of the circle) or flare out as with the implant 20.

In general (whatever the shape of the implant), the posterior edge needs to be far enough away from the anterior edge in order to afford an effective separating effect. In practice, the posterior edge is at a distance of at least 3 mm away from the anterior edge.

In general (whatever the shape of the implant), the length of the posterior edge does not exceed the length of the anterior edge by more than 10%.

However, according to alternative forms which have not been depicted, other implants exhibiting different shapes and/or dimensions may also suit: thus, an implant may extend over a larger circumference (or angular sector) around the cornea 12 than has been depicted in FIG. 1.

It will be noted that, in general (whatever the shape of the implant) the length of the anterior edge (portion of a circumference of a circle) is for example comprised between 3 and 7 mm. Beyond that length, the implant proves more difficult to insert (larger size of the incision, etc.).

The effect afforded by an implant in the general sense of the invention (increasing physiological uveo-scleral flow) may be obtained with one or several implants arranged around the cornea, one against another or alternatively separated from one another.

In general (whatever the shape of the implant), the various edges or faces or edge faces or flanks delimiting the exterior surface of the implant and which are adjacent to one another are joined together by angles of intersection, angles or corners which are rounded. In other words, the body of the implant has no sharp edges.

As indicated above, the body of the implant also has a thickness that is uniform and, when viewed in three-dimensions, has at rest a planar shape (the body does not have a second curvature in a direction perpendicular to a plane defined by the two dimensions of the body when viewed from above as in FIG. 1) or a curved shape (there is at least one second curvature present in this direction perpendicular to the plane of the other two dimensions).

Figure 2A:
FIGS. 2a to 2c illustrate various possible forms of embodiment of implants according to the invention.

FIG. 2a illustrates an implant 50 viewed in the direction of its thickness denoted "e", namely in a direction that is comprised in the plane of FIG. 1. Such an implant has a concave anterior edge, the concavity of which cannot be seen here.

This implant therefore comprises the concave curvature of the anterior edge in a plane defined by the other two dimensions of the body (excluding its thickness) but, at rest (in the non-deformed state) it is planar in a direction perpendicular to this plane (absence of second curvature).

The body of this implant is made from an elastically deformable material so that it can be bent without inducing permanent deformation so that it can be handled with a microinstrument, or injected using an ophthalmological injection system. When such a body is no longer subjected to a bending force, it reverts to its non-deformed original (rest) position.

Figure 2B:
Figure 2C:
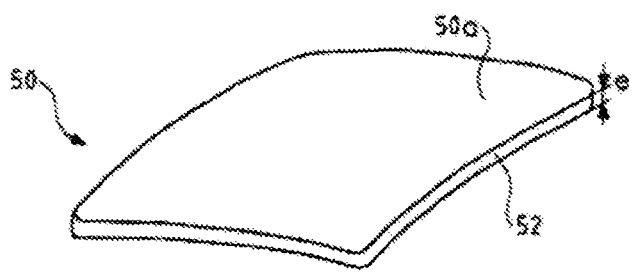

FIGS. 2b and 2c illustrate the body of FIG. 2a in a deformed state (FIG. 2b: profile view in the direction of the thickness; FIG. 2c: perspective view from above), for example when it has been implanted between the sclera and the uveal tissue. This deformed state may also be obtained when an external bending force is imposed on the body by a tool such as a micro instrument or an ophthalmological injection system for injecting.

The body as depicted in FIG. 2c conforms to a portion of a spherical surface and has the overall shape of a spherical cap portion. The shape of the body is therefore particularly well suited to conforming to a portion of the spherical surface of the ciliary body underlying the implant. This body comprises the concave anterior edge 52.

The shape adopted by the body in this deformed state shows that this body comprises (in addition to the concave curvature of the anterior edge) a double curvature in a direction perpendicular to the plane defined by the other two dimensions (length and width) of the body which are illustrated in FIG. 1. In FIG. 2b, just one of these other curvatures c (in addition to the concave curvature of the anterior edge) is depicted.

Thus deformed, the body comprises two large opposite faces separated from one another along the thickness: one convex upper face 50a which is doubly curved and a concave opposite lower face, not depicted, which is also doubly curved and which is intended to conform to a portion of a spherical surface. This double curvature allows the implant to correctly spread the separating effect between the tissues.

The convex upper face 50a is intended to face the sclera, whereas the concave lower face is intended to face the uveal tissue.

It will be noted that each curvature of the aforementioned double curvature has the same radius of curvature comprised between 10 and 15 mm and, for example, equal to 11 mm.

The body of the implant is made from a material that has a Young's modulus comprised between 30 and 60 kg/cm$^2$. Such a modulus gives the body a flexibility characteristic that allows it to deform elastically when inserted into the eye and then be kept in a permanently deformed state by the overlying and underlying structures of the eye, conforming to the natural curvature of these structures. Such a modulus makes it possible not to cause either one of these structures deformations which could be liable to impair their function(s).

In one exemplary embodiment, the Young's modulus is equal to 40 kg/cm$^2$ for an elastically deformable body made from a hydrophilic acrylic material which is, for example, hydrophilic to 25%.

It will be noted that everything that has been stated with regard to the embodiment of FIGS. 2a-c also applies to an implant the body of which has a different overall shape.

The contour of the body, viewed in projection in a plane defined by the two largest dimensions as in FIG. 1 (or in other words, a plane perpendicular to the thickness), may differ from that illustrated in FIG. 2c, with the exception of the anterior edge 52 which remains concave.

Moreover, it is possible for the anterior edge not to be thinned as in FIG. 2a.

Although FIGS. 2a-c the edges, flanks or edge faces of the body which extend in the thickness direction of the body appear to have sharp edges where adjacent faces meet, that is not the case. All these edges are rounded whatever the geometric orientation, so as to make the implant easier to insert.

According to an alternative form of embodiment, the body of the implant is made from a material which is not elastically deformable and which permanently has at least one second curvature c in the direction perpendicular to the plane of the other two dimensions (width and length in FIG. 1), as illustrated in FIG. 2b.

This other curvature is therefore present when the body is at rest. Once implanted in its final position of permanent interposition between the sclera and the uveal tissue, the body does not deform any further and maintains this other permanent curvature.

It will be noted that, according to this alternative form, the body may adopt the overall shape of FIG. 2c or a different overall shape as explained hereinabove in respect of the alternative forms applied to FIGS. 2a-c.

One example of a material that is not elastically deformable that may be used, is polysiloxane.

The body of the implant has, in a view in a plane containing the projections of the two longest dimensions of said body, namely the plane of FIG. 1, dimensions which are generally comprised between minimum dimensions of 2×2 mm and maximum dimensions of 7×7 mm. Such dimensions allow the implant to perform the necessary action to increase the physiological uveo-scleral flow which, in the absence of the invention, is approximately 10% in a human eye. This makes it possible to reduce the intraocular pressure.

These dimensions are sufficient for the effect of separating the tissues to be effective and for the resistance to flow of aqueous humor thus to be reduced, and are not so high as to disturb the dynamics of this flow. The implant as illustrated in FIG. 2c thus makes it possible to obtain a physiological uveo-scleral flow of around 30 to 40%, making it possible to reduce the intraocular pressure (IOP) considerably.

In FIGS. 2a and 2b the thickness of the body has been depicted as identical over the entire body.

However, the concave anterior edge may be thinned.

In the example of FIG. 2a (although this would also apply to FIGS. 2b and 2c) the concave anterior edge 52 has been depicted as thinned over a distance or dimension "I" which is comprised between 100 and 400 μm. This dimension is measured in a direction extending between the two opposite anterior 52 and posterior 54 edges of the body. The thinned portion is denoted 55. The remaining portion, denoted 57, of the body, of length "L" has, for example, an identical thickness that remains constant as far as the posterior edge inclusive.

However, according to an alternative form which has not been depicted, the thickness of the remaining portion of the body of length "L" has a value that is not necessarily uniform over all or part of this length.

In general (whatever the shape of the implant), the thickness of the posterior edge is at least equal to that of the anterior edge.

It will be noted that the uniform thickness of the body of the implant is generally comprised between 50 and 400 μm, thus affording sufficient and effective separation of the tissues. Below 50 μm the separation effect exists little if at all. Above 400 μm, there is a conceivable risk of hypotonia.

The length I of thinning of the anterior edge (portion 55) affords good results in terms of the effectiveness of positioning of the implant as close as possible to the trabeculum, without, however, disturbing the structure of the scleral spur and therefore its insertion on the ciliary body.

The body of the implant has a volume comprised between 0.8 and 8 mm$^3$, allowing it to ensure the desired uveo-scleral flow without giving rise to problems of unacceptable deformation of the overlying and underlying tissues and disturbance of the dynamics of the aqueous humor.

FIGS. 3 to 5 illustrate another aspect of an implant according to another embodiment of the invention and depict three implants 60, 70 and 80 viewed in profile, which means to say in the direction of their thickness. For the sake of simplicity, these figures do not depict any curvature such as the curvature(s) illustrated in FIGS. 2b and 2c. However, the description which follows applies to implants of which the body is or is not elastically deformable, with simple or double curvature in the direction of the thickness and irrespective of the shape and dimensions of the implant. In FIGS. 3 to 5, the dimensions have been deliberately exaggerated for the sake of understanding.

According to this aspect, the body of the implant is able to allow liquid flow of aqueous humor through said body (FIG. 3) or along it (FIG. 4), or even through and also along the body (FIG. 5). Specifically, the implant which is interposed between the ciliary body and the sclera needs to encourage the flow/drainage of the aqueous humor collected at the trabeculum toward the posterior part of the eye. This flow may be encouraged along the body (from its anterior edge to its opposite posterior edge) and/or through the body.

As illustrated in FIG. 3, the body of the implant 60 is pierced with orifices 62 passing through its thickness. These orifices 62 allow aqueous humor to flow through the body, from one of its two large opposite faces 60a to the other large opposite face 60b. The orifices are depicted here as being aligned in a direction extending from the concave anterior edge 64 to the opposite posterior edge 66 in a plane of section. The body is also pierced with a plurality of other orifices, not depicted, which are situated in other planes in front of and behind the plane of section of FIG. 3.

However, the orifices passing through the body are not necessarily aligned as illustrated in FIG. 3. By way of example, each orifice has a diameter of 50 μm and the thickness of the body is 200 μm.

As illustrated in FIG. 4, the body of the implant 70 comprises, on at least one of its two large opposite faces 70a, 70b, a relief which is able to encourage a flow of aqueous humor along said at least one large face.

In the example depicted, the two large faces 70a and 70b are provided with such a relief which, as can be seen, is not necessarily identical from one face to the other. However, this relief could be the same from one face to the other.

The relief for example adopts the form of grooves or channels 72, 74 formed respectively on the faces 70a, 70b, at the surface thereof. These grooves or channels 72, 74 are preferably aligned substantially parallel to a direction extending from the concave anterior edge of the body to the opposite posterior edge thereof.

In FIG. 4, this direction is perpendicular to the plane of the figure, the anterior and posterior edges not having been depicted. Only the opposite adjacent edges s 76, 78 are depicted.

In order not to weaken the constitution of the body by locally reducing each thickness wherever two grooves or channels might face one another, the grooves or channels 72 are not arranged facing the grooves or channels 74.

It will be noted that the body of the implant may combine the through-orifices and the grooves: the orifices are, for example, placed in the bottoms of the grooves or between two adjacent grooves arranged on one and the same face.

The implant 80 of FIG. 5 comprises, created on the large face 80a, grooves or channels 82 and, offset therefrom, formed on the opposite large face 80b, grooves or channels 84. Through-orifices 89 are made in the thickness of the body, at various places, between the grooves of the two faces and/or on each side of the grooves. The number, size and location of the grooves and of the orifices may vary.

As in FIG. 4, the grooves of the two opposite faces are arranged in a staggered configuration, for the same reasons.

In FIG. 5, the anterior and posterior edges have not been depicted, as in FIG. 4, only the opposite adjacent edges 86, 88 having been depicted.

According to an alternative form which has not been depicted, the relief may adopt the shape of a roughness or texture given to one and/or the other of one of the two large opposite faces of the body by a known method.

More generally and this has not been depicted, an implant according to an alternative form of the implant of FIG. 5 incorporates both the through-orifices and a relief which differs from the aforementioned grooves or channels. It being possible for this relief to be the same or to vary from one place to the other.

It will be noted that the relief described hereinabove in conjunction with FIGS. 4 and 5 may be likened to local variations in thickness of between 10 and 20 µm on each (or just one) of the two large opposite faces of the body. These local variations in thickness occur in one or two dimensions perpendicular to the thickness which dimensions are small in comparison with the dimension or dimensions of the body perpendicular to the thickness (approximately 10 times smaller than the dimension or dimensions). It will be noted that the variation in thickness is of the order of 10% of the uniform overall thickness of the body. Thus, the body illustrated in FIGS. 4 and 5 has a thickness that is substantially uniform, which means to say a thickness that has a given nominal or overall value and which locally tolerates variations in thickness of between 10 and 20 µm.

In general, the material or materials of which the body of the implant is made are chosen from the following materials: PTFE, polysiloxane, hydrophilic or hydrophobic acrylate hydrogels.

The body of the implant has properties of releasing one or more substances. Such substances are, for example, anti-infection and/or anti-inflammatory substances. They may be antibiotic and/or cortisone or anti-cortisone substances.

Figure 6:
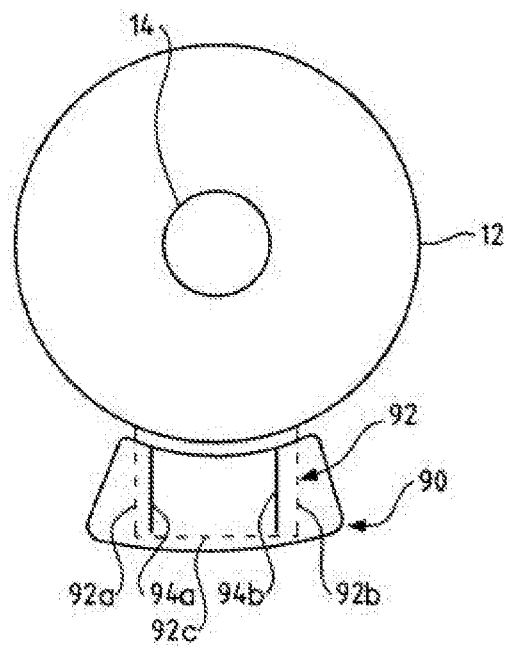
FIGS. 6 and 7 very schematically illustrate the installation of an implant according to two different methods.

FIG. 6 illustrates the insertion of an implant 90 using a first method of implantation according to one embodiment of the invention. This first method is used in addition to conventional anti-glaucoma surgical intervention or in addition to any intraocular intervention when a lowering of the intraocular pressure is desirable. The trabeculotomy and the sclerotomy entail cutting one or several scleral flaps in the eye which flaps will be lifted in order to continue with the intervention. A scleral flap 92 (illustrated in dotted line in FIG. 6) is obtained by making an incision in the sclera in one or two planes and to a variable depth, along three sides: two incisions 92a, 92b substantially parallel to one another extending from the cornea 12 away from the latter, and a third incision 92c perpendicular to the other two incisions and a distance away from the cornea. The three-incision cut thus made forms what is known as one or several scleral flap(s). After the scleral flap(s) has(have) been lifted, two incisions (94a, 94b in FIG. 6) are made as far as the ciliary body, inside the flap 92, so that the implant can be slipped in between the deep scleral plane and the ciliary body. By way of example, the incisions are spaced at least 2 mm apart.

According to an alternative form which has not been depicted, a single incision in the deep scleral plane is made in order to achieve the same objective.

The implantation method used then comprises a step of introducing a viscoelastic substance, for example of the hyaluronic acid type, through at least one of the incisions made, between the sclera and the ciliary body, so as to separate these two tissues which were previously stuck together. This will allow the implant to be inserted without trauma to the overlying and underlying structures.

This step is performed using an injection instrument such as an injection canula with a diameter of the order of 20 to 30 g.

A small quantity of substance, for example 0.05 mm$^3$, is injected.

The implantation method also comprises a step of introducing an instrument such as soft-ended forceps, through one of the two incisions 94a, 94b extending depthwise as far as the ciliary body. The forceps reemerge via the second incision and grasp the implant so as to place it between the sclera and the ciliary body.

During a subsequent step, using a microsurgery instrument such as a blunt-edged spatula the implant 90 is positioned as close as possible to the trabeculum (so that it is concentric with the corneal margin), as explained above, so as to collect the maximum of aqueous humor.

Another type of instrument or device that allows the implant to be installed, deployed and positioned in the space situated between the sclera and the ciliary body (in the suprachoroidal space) can be used, such as an injector.

During another step, the scleral flap or flaps are folded down and may or may not be sutured.

Figure 7:
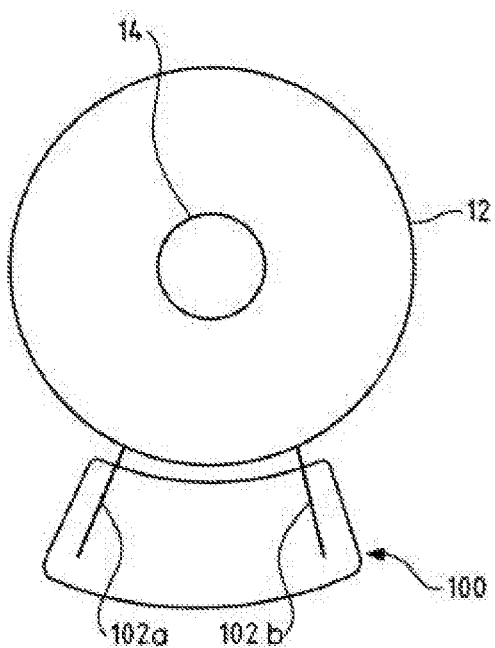

FIG. 7 illustrates the installation of an implant 100 using a second implantation method according to one embodiment of the invention.

This method is very similar to the first method except for the fact that the second method is not used in addition to a conventional intervention but in itself constitutes an intervention.

According to this method:

two incisions 102a, 102b which are radial with respect to the cornea or mutually parallel (like the incisions 94a, 94b of FIG. 6) are made from the corneal margin (the zone marking the transition between the cornea and the sclera) over a length ranging for example from 1 to 4 mm, and are continued as far as the ciliary body, a viscoelastic substance, for example of the hyaluronic acid type, is injected through one of the two incisions, the sclera is lifted so as to allow the implant 100 to be inserted and placed.

These steps are identical to those described hereinabove for the first method.

The final step of suturing the incisions is still optional.

According to an alternative form of embodiment which has not been depicted, one single incision is made during this second method and is sufficient to install an implant in a position of interposition between the sclera and the ciliary body.

It will be noted that the implants 90 and 100 depicted in FIGS. 6 and 7 may be any one of the implants described hereinabove. The implant insertion methods described hereinabove apply to any implant according to the invention and notably to a permanent interpositional ophthalmological implant between the sclera and the uveal tissue which comprises a uveo-compatible thin body formed of a single piece, the body having a substantially uniform single thickness e which is at least smaller than 10 times the smallest of the other two dimensions of the body, the body of the implant comprising two opposite edges which are distant from one another along one of the two dimensions perpendicular to the thickness, the one of the edges referred to as the anterior edge having, in projection in a plane perpendicular to the thickness, a concave curvature facing toward the outside of the body. The implant may further comprise any one (or several or even all) of the features set out in the general description and in the various embodiments and alternative forms.

The second method described applies to the insertion of several implants according to the invention. In general, at least one different incision (or even two in the example of FIG. 7) needs to be made for the insertion of each different implant.

Figure 8:
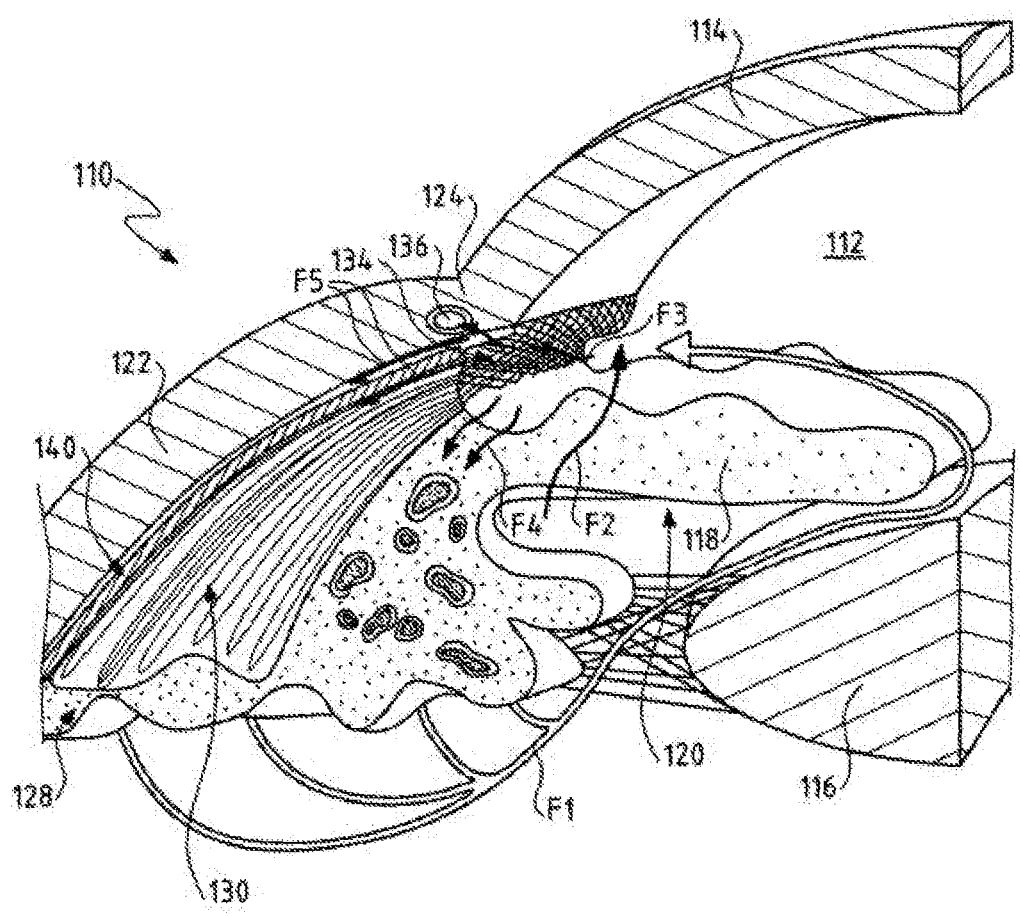
FIG. 8 is a schematized view of the placement in a human eye of one possible form of embodiment of an implant according to the invention which is interposed between the sclera and the ciliary body.

FIG. 8 depicts, in cross section, an implant according to an embodiment of the invention which has been inserted using one of the methods described hereinabove.

This section through part of an eye 110 depicts the anterior chamber 112 which lies between the cornea 114 and the lens 116 delimited at its peripheral part by the iris 118.

Behind the iris 118 is the posterior chamber 120.

The sclera 122 is connected to the periphery of the cornea 114 via the corneal margin 124 (region of change in radius of curvature between the sclera and the cornea). The sclera 122 covers the ciliary body 128 which is connected to the iris 118 and which contains the ciliary muscle 130 on which the sclera 122 rests.

The trabeculum 134 positioned between the cornea and the iris acts as a filter and is passed-through by the aqueous humor which circulates in the anterior chamber 112.

The Schlemm's canal 136 is situated between the sclera and the cornea behind the trabeculum 134.

The various arrows F1, F2, F3 and F4 illustrate the paths or routes followed by the aqueous humor:

F1 represents the conventional path or flow followed by the aqueous humor entering the anterior chamber 112;

F2 represents the diffusion path or flow followed by the aqueous humor to enter the anterior chamber 112;

F3 represents the conventional path or flow followed by the aqueous humor leaving the anterior chamber 112 through the trabeculum 134 and heading toward the Schlemm's canal 136;

F4 represents the conventional physiological uveo-scleral flow of the aqueous humor leaving the anterior chamber 112.

Figure 9:
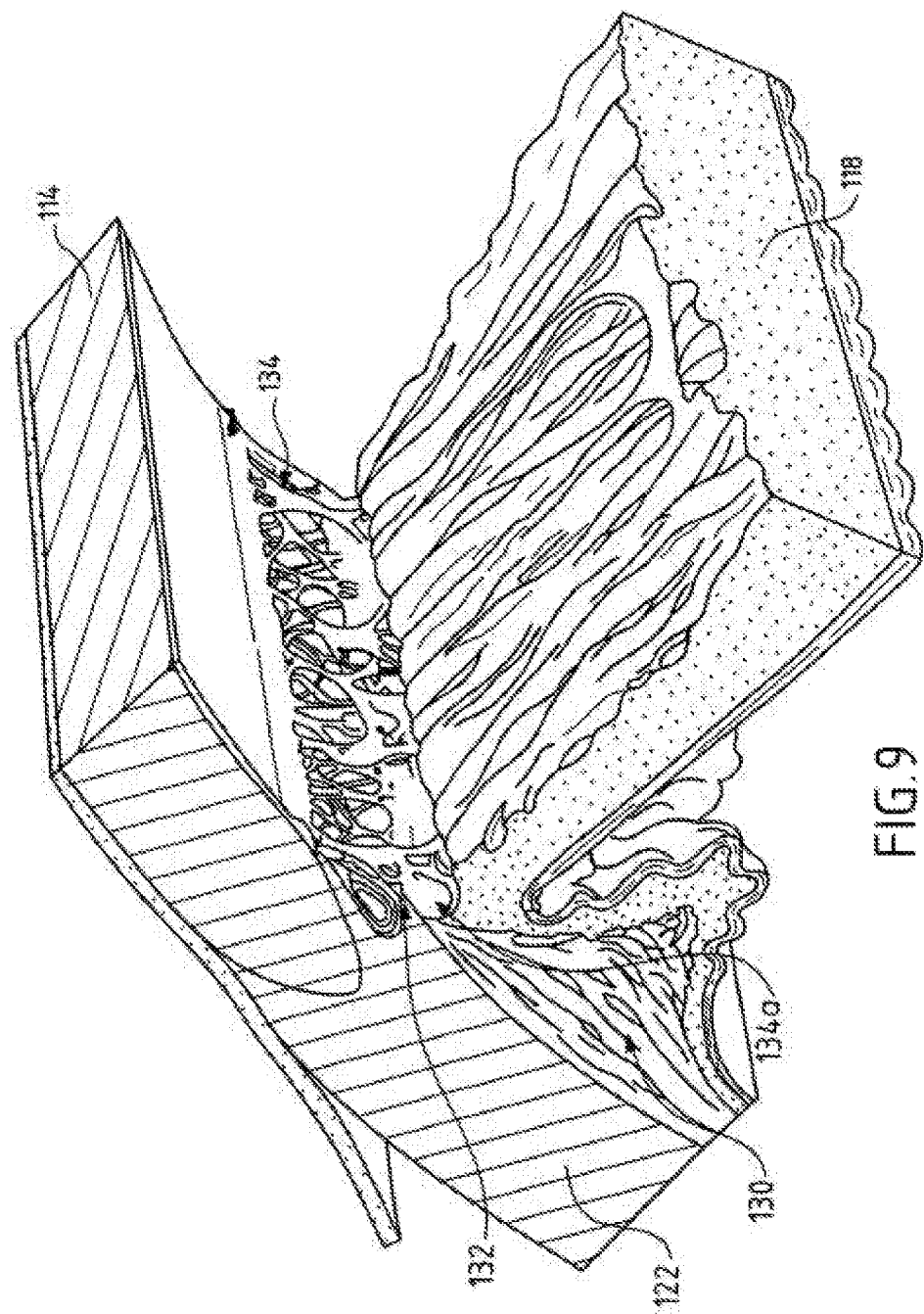
FIG. 9 is a more detailed and enlarged view of the structure of the iridocorneal angle without the implant of FIG. 8.

An implant 140 according to one embodiment of the invention has been interposed between the sclera 122 and the ciliary muscle 130 as described hereinabove. This implant is positioned as close as possible to the trabeculum (thanks to its concave anterior edge) so that it can perform its permanent separation effect at the most appropriate point while at the same time respecting the insertion of the ciliary muscle 130 on the scleral spur. FIG. 9 is a more detailed and enlarged view of the structure of the iridocorneal angle without the implant. As depicted in this figure, the scleral spur 132 on which the ciliary muscle 130 is inserted is situated above the posterior part 134a of the trabeculum 134.

The separation produced at this point between the sclera and the ciliary body allows the aqueous humor to be constantly collected as close as possible to the zone of physiological uveo-scleral flow (the separation effect creates a zone of lesser resistance to flow of the aqueous humor).

Such an implant thus positioned affords a significant gain in the increase in the physiological uveo-scleral flow.

The physiological uveo-scleral flow is increased by an additional fraction of flow through the posterior part of the trabeculum (the ciliary trabeculum), as indicated in FIG. 8 by the arrows F5 situated above and below the implant. The flow of this additional fraction is obtained thanks to the separating effect of the implant separating the sclera and the ciliary body, as close as possible to the trabeculum without, however, damaging the latter.

Figures 10A, 10B:
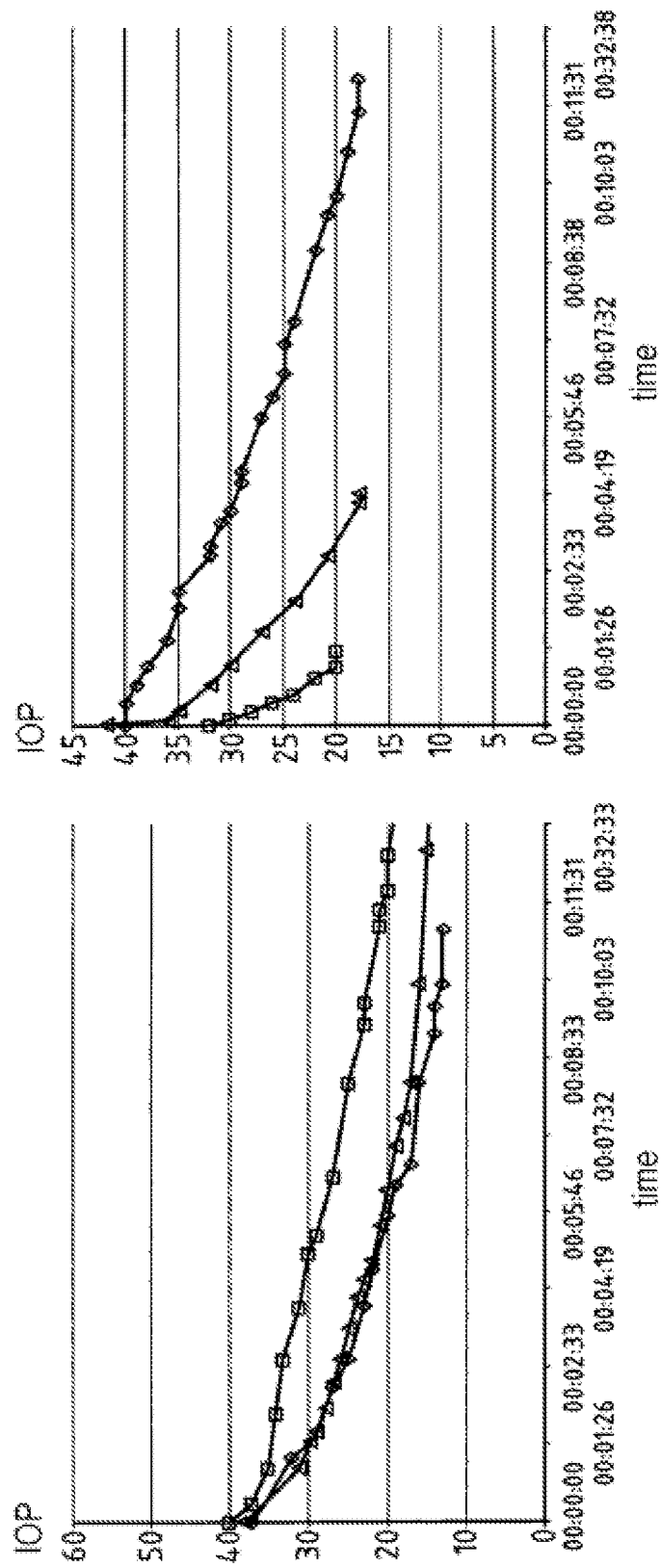
FIGS. 10a and 10b are comparative views showing the improvement in the flow of aqueous humor in the presence of an implant according to one embodiment of the invention between the sclera and the uvea.

FIGS. 10a and 10b illustrate the results of an experiment carried out on an eye from the eye bank that cannot be used for corneal grafts.

A 15 g weight corresponding to an intraocular pressure (IOP) simulating the conditions of glaucoma was placed on the top of the cornea of the eye.

A pressure sensor was placed inside the eye to measure the IOP. Successive IOP (tonography) measurements were recorded on the eye without the implant and then with the implant, such as to measure any effects the implant might have on the flow of aqueous humor and therefore on the IOP.

An implant according to the invention, notably according to one embodiment of the invention, was inserted into the eye through two scleral incisions using the surgical implantation method described with reference to FIG. 7. The implant was introduced into the supra-ciliary space.

The implant in question is an implant with dimensions 5×3 mm, 150 µm thick, made from a 25% hydrophilic acrylic material known for its uveo-compatibility. The shape of the implant is that of the implant 30 of FIG. 1.

Successive IOP measurements were taken and recorded (in mm Hg), here over 12 minutes, so as to identify the ease with which the aqueous humor flows. This technique is known by the name of tonography. This technique is described for example in the following reference: J Glaucoma. 2003 June;12(3):237-42 "Tonography demonstrates reduced facility of outflow of aqueous humor in myocilin mutation carriers", Wilkinson C H 1, Van der Straaten D, Craig J E, Coote M A, McCartney P J, Stankovitch J, Stone E M, Mackey D A.

Various curves of results of measurements illustrated in FIG. 10a (curves bearing squares, triangles and diamonds) are those obtained on the eye without an implant by exerting different local pressures on the eye. The different pressures exerted simulate variations in IOP as may be encountered in glaucoma and the consequences these have on the flow. The two curves with the squares and the triangles are those for which the local pressures were exerted.

Various curves of results of measurements which are illustrated in FIG. 10b (curves bearing squares, triangles and diamonds) are those obtained on the eye with the aforementioned implant by exerting different local pressures on the eye (curves with squares and triangles).

Comparing the corresponding curves between the two figures shows that the curves of FIG. 10b have steeper slopes (greater IOP gradient) than those of FIG. 10a and thus that the time taken for the IOP to return to a physiological pressure of between 10 and 20 mm Hg is shorter.

The greater speed at which a physiological IOP is reestablished with an implant according to the invention means that the flow of aqueous humor has been improved very significantly.

The inversion of the curves between FIGS. 10a and 10b stems from the fact that, in the presence of the implant, the flow is greater with a higher exerted pressure.

The invention claimed is:

1. A permanent interpositional ophthalmological implant between the sclera and the uveal tissue, comprising a body with uveal biocompatibility, formed as a single part, the thin body having three dimensions in space, namely a length and a width which are perpendicular to a thickness, the thin body having a substantially uniform single thickness which is at least less than 10 times the smaller of the other two dimensions of the body, the body of the implant comprising an anterior edge and an opposite edge which are distant from one another along a smaller of the two dimensions perpendicular to the thickness, the anterior edge facing the anterior chamber when disposed between the sclera and the uveal tissue having, in projection in a plane perpendicular to the thickness, a concave curvature facing toward the outside of the body, the body of the implant being configured to allow a liquid flow of aqueous humor through said body and/or along the same from its anterior edge to its opposite posterior edge.

2. The interpositional ophthalmological implant as claimed in claim 1 wherein the concave anterior edge is thinned over a dimension comprised between 100 and 400 μm, this dimension being considered in a direction extending between the two opposite edges of the body.

3. The interpositional ophthalmological implant as claimed in claim 1, wherein the concave curvature of the anterior edge has a radius of curvature between 5 and 7 mm.

4. The interpositional ophthalmological implant as claimed in claim 1, wherein the body of the implant is elastically deformable so that it can be bent without inducing permanent deformation so that it can be handled using a micro instrument, or injected using an ophthalmological injection system.

5. The interpositional ophthalmological implant as claimed in claim 4, wherein the body of the implant comprises, in a deformed state in which it is capable of being used as an interpositional ophthalmological implant between the sclera and the uveal tissue, a second concave curvature in a direction perpendicular to a plane defined by the two dimensions of the implant which are perpendicular to the thickness (e).

6. The interpositional ophthalmological implant as claimed in claim 5, wherein the second concave curvature has a radius of curvature of between 10 and 15 mm.

7. The interpositional ophthalmological implant as claimed in claim 5, wherein the body of the implant has, in a three-dimensional view, the overall shape of a spherical cap portion.

8. The interpositional ophthalmological implant as claimed in claim 1, wherein the body of the implant is made from a material which has a Young's modulus of between 30 and 60 kg/cm$^2$.

9. The interpositional ophthalmological implant as claimed in claim 1, wherein the body of the implant is not elastically deformable and permanently comprises another concave curvature in a direction perpendicular to a plane defined by the two dimensions of the implant which are perpendicular to the thickness.

10. The interpositional ophthalmological implant as claimed in claim 1, wherein the body of the implant has two large opposite faces separated from one another along the thickness of the body.

11. The interpositional ophthalmological implant as claimed in claim 10, wherein the two large opposite faces are substantially planar or curved.

12. The interpositional ophthalmological implant as claimed in claim 11, wherein the two large opposite faces each have one or several local variations in thickness of between 10 and 20 μm.

13. The interpositional ophthalmological implant as claimed in claim 10, wherein the body of the implant is pierced with orifices passing through its thickness.

14. The interpositional ophthalmological implant as claimed in claim 10, wherein the body of the implant comprises, on at least one of its two large opposite faces a relief which is able to encourage a flow of aqueous humor along said at least one large face.

15. The interpositional ophthalmological implant as claimed in claim 14, wherein the relief on said at least one large face of the body takes the form of grooves formed on said at least one large face or of roughness conferred thereon.

16. The interpositional ophthalmological implant as claimed in claim 1, wherein the body of the implant comprises at least one material chosen from the following materials: PTFE, polysiloxane, hydrophilic or hydrophobic acrylate hydrogels.

17. The interpositional ophthalmological implant as claimed in claim 1, wherein the body of the implant has, when viewed in a plane containing the projections of the two largest dimensions of said body, dimensions comprised between minimum dimensions of 2×2 mm and maximum dimensions of 7×7 mm.

18. The interpositional ophthalmological implant as claimed in claim 1, wherein the thickness (e) of the body of the implant is between 50 and 400 μm.

19. The interpositional ophthalmological implant as claimed in claim 1, wherein the body of the implant has a volume of between 0.8 and 8 mm$^3$.

20. The interpositional ophthalmological implant as claimed in claim 1, wherein the body of the implant has properties of releasing one or more substances.

21. The interpositional ophthalmological implant as claimed in claim 1, wherein the body has an external surface which exhibits neither sharp edges nor sharp corners.

22. The interpositional ophthalmological implant as claimed in claim 1, the body has, viewed in projection in a plane perpendicular to the thickness, four edges delimiting the outline of said body: the anterior edge and the opposite posterior edge, and two lateral edges adjacent to said anterior and posterior edges and which connect the latter edges to one another.

23. The interpositional ophthalmological implant as claimed in claim 22, wherein the two lateral edges converge toward one another in a direction leading from the posterior edge toward the anterior edge, or are mutually parallel.

24. The interpositional ophthalmological implant as claimed in claim 23 wherein the body has, viewed in projection in a plane perpendicular to the thickness, the overall shape of an annular segment.

25. The interpositional ophthalmological implant as claimed in claim 1, wherein the body has, in projection in a plane perpendicular to the thickness, an external peripheral contour with a convex geometry with the exception of the portion of the body which comprises the concave anterior edge.

26. The interpositional ophthalmological implant as claimed in claim 1, wherein the other of the two opposite edges is a posterior edge, the posterior edge being at a distance of at least 3 mm away from the anterior edge.

27. A method for inserting a permanent interpositional ophthalmological implant of claim 1 between a sclera and an uveal tissue in an eye of a patient, the method takes place after a conventional intraocular surgical intervention has been performed on the eye of the patient and cutting one or several scleral flaps in said eye of the patient has been made, the method comprising:

lifting the one or several scleral flaps;

making at least one incision as far as the ciliary body;

inserting the implant between the sclera and the ciliary body;

positioning the implant as close as possible to the trabeculum so that it is concentric with the corneal margin in order to collect a maximum of aqueous humor.

28. The method of claim 27, wherein, before inserting the implant, the method further comprises injecting a viscoelastic substance through said at least one incision between the sclera and the ciliary body so as to separate these two tissues.

29. The method of claim 27, wherein positioning the implant as close as possible to the trabeculum further comprises positioning the concave curvature of the anterior edge as close as possible to the trabeculum.

30. The method of claim 29, wherein positioning the implant as close as possible to the trabeculum further comprises positioning the concave curvature of the anterior edge as close as possible to the trabeculum.

31. A method for inserting a permanent interpositional ophthalmological implant of claim 1 between a sclera and an uveal tissue in an eye of a patient, the method comprising:

making at least one radial incision with respect to the cornea, the at least one incision being made from the corneal margin and continued as far as the ciliary body;

inserting the implant between the sclera and the ciliary body;

positioning the implant as close as possible to the trabeculum so that it is concentric with the corneal margin in order to collect a maximum of aqueous humor.

32. The method of claim 31, wherein, before inserting the implant, the method further comprises injecting a viscoelastic substance through said at least one radial incision between the sclera and the ciliary body so as to separate these two tissues.

* * * * *